United States Patent

Cornforth

[11] 3,961,523
[45] June 8, 1976

[54] SCANNING ULTRASONIC INSPECTION METHOD AND APPARATUS

[75] Inventor: Alexander Rankin Cornforth, Stanion, England

[73] Assignee: British Steel Corporation, London, England

[22] Filed: June 17, 1974

[21] Appl. No.: 479,707

[30] Foreign Application Priority Data
June 19, 1973 United Kingdom............. 29053/73

[52] U.S. Cl................................. 73/67.8 S; 73/67.9
[51] Int. Cl.² ........................................ G01N 29/04
[58] Field of Search............. 73/67.8 R, 67.8 S, 67.9

[56] References Cited
UNITED STATES PATENTS
| | | | |
|---|---|---|---|
| 3,221,544 | 12/1965 | Gunkel | 73/67.8 S |
| 3,260,105 | 7/1966 | McNulty | 73/67.9 |
| 3,415,110 | 12/1968 | Cowan | 73/67.8 S |
| 3,570,279 | 3/1971 | Davies | 73/67.9 |

OTHER PUBLICATIONS
Cornforth & Lewis, Automatic Inspection of Steel Tubes, Conference: Ultrasonics for Industry 1969, Conference Papers, London, England, Oct. 7–8, 1969.

Primary Examiner—Richard C. Queisser
Assistant Examiner—John P. Beauchamp
Attorney, Agent, or Firm—Nolte and Nolte

[57] ABSTRACT

An arrangement for testing tube-like articles for defects includes scanning a defect detecting device in a helical path about the article; marking, upon receipt of defect indicative signals at the device, a pictorial record of the magnitude and position along the article of defects shown by the received defect indicative signals if they are greater than a predetermined magnitude; subjecting received defect indicative signals greater than said predetermined magnitude to predetermined repetition tests; and marking on the pictorial record the circumferential position about the article of defects shown by the received defect indicative signals if they satisfy the predetermined repetition tests.

17 Claims, 5 Drawing Figures

SCANNING ULTRASONIC INSPECTION METHOD AND APPARATUS

This invention relates to the testing of articles and more particularly to the non-destructive testing of tubular or rod or bar like articles, such as steel tubes, for defects.

According to one aspect of the present invention there is provided a method of testing tubular, rod or bar like articles for defects comprising scanning a defect detecting device in a helical path about the article; marking, after the receipt of defect indicative signals at the device, a pictorial record of the magnitude and position along the article of defects shown by the received defect indicative signals subjecting the received defect indicative signals if they are greater than a predetermined magnitude to predetermined repetition tests; and marking on the pictorial record the circumferential position about the article of defects shown by the received defect indicative signals if they satisfy the predetermined repetition tests.

The invention may also include the step of marking the article (with paint for example) to indicate the longitudinal and circumferential position of received defect indicative signals if they satisfy the predetermined tests.

According to another aspect of the present invention there is provided apparatus for testing tubular, rod or bar like articles for defects comprising a defect detecting device adapted for helical scanning about the article to be tested; means for marking, upon receipt of defect indicative signals at the device, a pictorial record of the magnitude and position along the article of defects shown by the received defect indicative signals; means for applying to the defect indicative signals if they are greater than a predetermined magnitude, predetermined repetition tests; and means for marking on the pictorial record the circumferential position about the article of defects shown by the received indicative signals if they satisfy the predetermined repetition tests.

The defect detection may be accomplished by means of ultrasonic pulse testing means.

In order that the invention may be more readily understood one embodiment thereof will now be described by way of example with reference to the accompanying drawings in which:

FIG. 5 is a block diagram of the pulse height discriminator and store portion of the arrangement illustrated in FIG. 1.

The ultrasonic rotating probe testing apparatus illustrated is specifically intended for the ultrasonic examination of seamless steel tube in the 4½ to 20 inches diameter range. The apparatus embodies an ultrasonic system for detecting the presence of predominantly longitudinally orientated discontinuities which are of an essentially circumferential nature. This is achieved using the "shearwave" pulse echo technique. The system incorporates eight ultrasonic transducers spaced at 90° intervals in pairs on a rotating annulus (not shown). Each pair consists of one probe facing inclined towards the direction of rotation, the other facing inclined against the direction of rotation. This arrangement of the probes is required to overcome discontinuity orientation effects, i.e., the discontinuities are examined from both sides as very often natural discontinuities are not radial to the surface. The eight ultrasonic probes are pulsed simultaneously at 8 KHz to ensure adequate circumferential coverage on the largest diameter at maximum rotational speed. The inspection pitch is dependent on the rotary head speed and the tube throughput speed, but it should be noted that although there are eight probes rotating around the tube, these eight can only be considered as four, as they are arranged in pairs as described above.

Normal customer specifications dictate that a shearwave test system should be calibrated to longitudinal parallel sided notches machined on the internal and external surfaces of a test pipe and these notches are specified typically as 5% of the nominal tube wall thickness. Most specifications only require a GO/NO GO output from the shear-wave system in order to operate a paint gun unit to mark the longitudinal position of detected discontinuities. The system illustrated not only meets these requirements but offers the facility of permanent record recording which also includes some novel ideas on signal processing and pictorial display.

Figure 1:
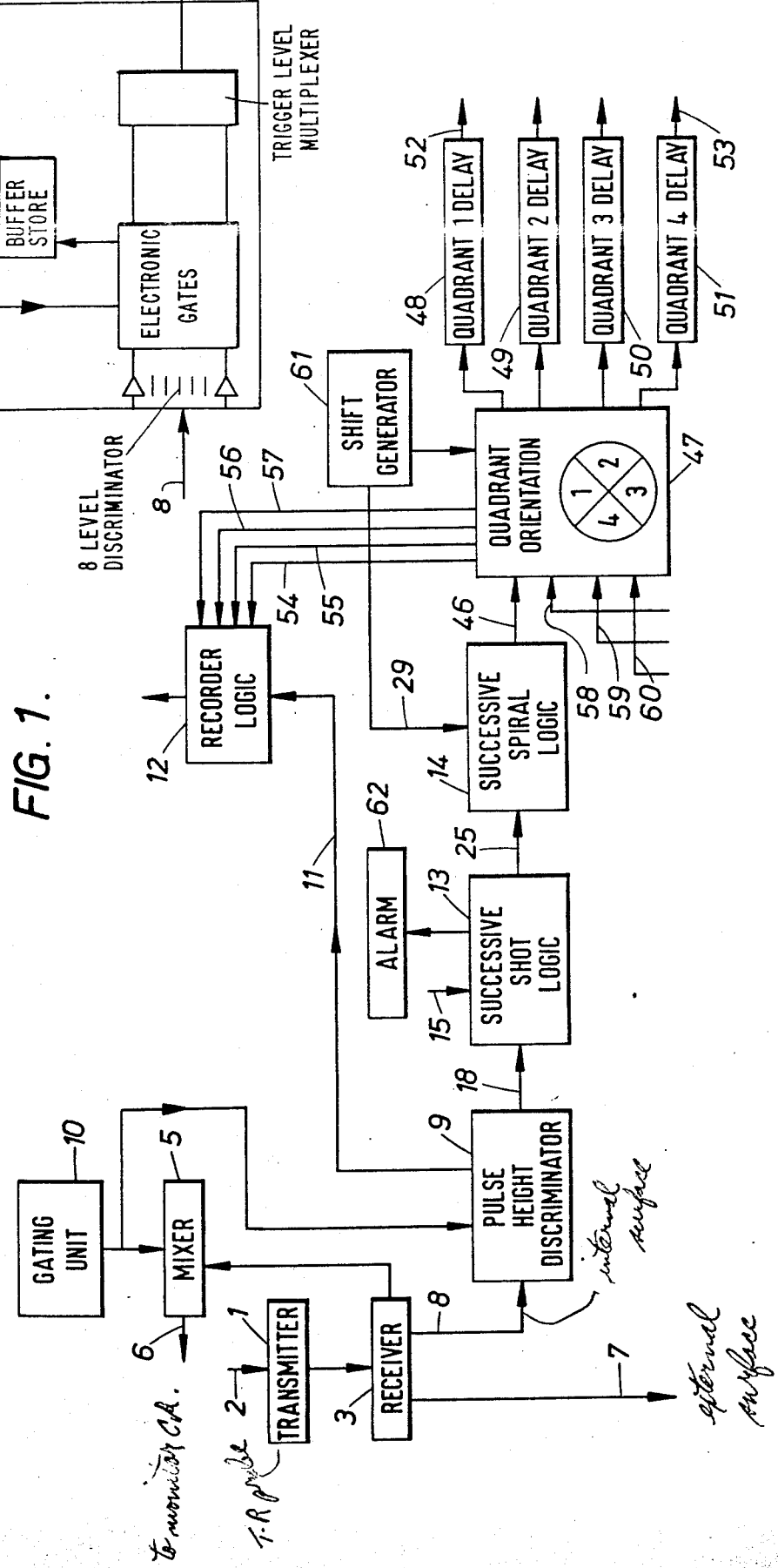
FIG. 1 is a block circuit diagram showing the operation of the arrangement.

The shearwave system to be described employs 8 pairs of identical channels, one of one pair of which is shown in some detail in FIG. 1.

Pulses are derived from a master oscillator to excite all eight shearwave probes simultaneously at a P.R.F. (pulse repetition frequency) of 8 KHz for tube wall thickness up to 1 inch, and at 4 KHz for wall thickness up to 2 inches. Considering the operation channel of probe 1, pulses from the master oscillator are fed to a transmitter 1 at input 2, whereby the transmitter is signalled to excite the ultrasonic probe on the rotating head. Signals returning to this probe are passed to a pre-amplifier in the transmitter 1, and then to a main amplifier via a 0 – 80 dB attenuator in a receiver 3. The output signal from the main amplifier is split into three lines as follows:

1. Signals to a mixer unit 5 having an output 6 connected to a monitoring oscilloscope
2. Signals at an output 7 relating to discontinuities in the external surface of the tube
3. Signals at an output 8 relating to discontinuities in the internal surface of the tube The operations of the logic for internal and external signals although separate, are identical and thus only the internal signal processing logic is described. It is to be noted that considering all eight shearwave channels there are thus 16 processing logic channels, i.e. eight for external signals and eight for internal signals.

The signal output from the main amplifier is passed to the main 'internal' signal processing logic via a balance control in the receiver 3 which allows the signal amplitude to be ajusted before processing. This facility is also available on the signal line 7 to the external signal processing logic. Using these balance controls, i.e., one for external and one for internal, the signal amplitudes received by the probe channel being described can be adjusted to be equal. This is described since it is often the case using identical machined 5% notches on the internal and external surfaces of a tube, that the signal response from these notches are not equal due to ultrasonic and tube geometry reasons. It is normal during the calibration procedure of the equipment to have one of the two balance controls on each channel at maximum having first established which of the two notches (internal or external) is giving the inferior signal response. That is, if the internal signal response is inferior to that of the external notch, the internal balance control would be at a maximum and the external signal amplitude adjusted to equal that from the internal notch when viewed on the recorder.

The first stage of the signal processing logic consists of a pulse height discriminator and store unit 9 is illustrated in FIG. 5. This unit accepts signals from the balance control in receiver 3 via line 8 and senses the amplitude of the signals by pulse height discrimination into eight levels of increasing amplitude. A gating waveform which is produced for each of the eight channels for both internal and external signal separation, is fed from a gating unit 10 to electronic gates at the output of the pulse height discriminator to allow all signals which have undergone pulse height sensing and which occur within the gating waveform period, to be passed by line 11 to an electrostatic recorder logic 12 via a buffer store and multiplexer in the discriminator 9. These gated signals, now in the form of eight discrete digital levels are also passed to a trigger level multiplexer within the discriminator 9 which is preprogrammed to pass only one of the discrete digital levels, this level (selectable between levels 1–10) being the trigger level. Signals exceeding this level will cause a digital output indication to be passed for further processing.

Signals which have occurred in the gated period and which are above the trigger level are passed to a unit 13 known as the 'successive shot logic' and if the conditions within this unit have been satisfied, a signal from this unit is fed to another unit 14 known as the 'successive spiral logic.' Some explanation of the need for these functions is necessary, as follows:

'SUCCESSIVE SHOT LOGIC'

An ultrasonic transducer rotating around a tube at a fixed RPM being pulsed at a constant PRF introduces a pulse of ultrasound into the tube wall at discrete intervals on the helical scan path. The distance between these intervals (which is fixed) is known as the circumferential coverage (or distance moved per shot). It is normal practice in the design of an ultrasonic rotary probe system to ensure that the PRF is as high as possible (dictated primarily by the maximum wall thickness of the tube to be inspected), and ensure that, although the rotational speed of the probes is high (in order to achieve maximum tube throughput speed) it is not so high that the distance moved per shot increases to the point that it is possible to miss the maximum signal amplitude response from a discontinuity. In a typical installation with the PRF at 8 KHz the RPM of the probes at 300, the distance moved per shot on a 16 inches o.d. pipe is given by:

$$C = \frac{\pi D \times RPM}{60 \times PRF}$$

where
D = pipe diameter in inches
RPM = rotational speed of probe in revs. per minute
PRF = pulse repetition frequency in Hz $$C = \pi \frac{16 \times 300}{60 \times 8000} = \frac{\pi}{100} = 0.03''$$

Thus with the quoted figures, a shot every 0.03 inch results. This ensures that as a probe beam passes through the object there will be a signal return on a number of shots from a discontinuity and the probability of receiving the maximum response is high.

Many shearwave systems operate on the basis of receiving one signal from a discontinuity, and if over a preset trigger level will operate external alarms etc. The main problems with such systems is that they have a poor noise immunity. To improve noise immunity (e.g., electrical noise due to contactor switching, etc., either line or air-borne) the system devised requires signals returning to the probe which occur in the gated period, and are above a pre-set level, to be present on a pre-set number of successive shots. In the present shearwave system, all signals in the gated period are recorded, but only those above the trigger level and which occur for a specified number of successive shots are allowed through the system. (Typical setting 3 or 4). The principal of operation is that signals fed to the successive shot logic 13 are checked by a series of gates which determine if gated signals have occurred successively, i.e., in successive gated periods. If so, a counter counts the number of successive signals received and if above a pre-set number (selectable on the equipment) a signal is passed to a store. An output on the store will result, output 'high,' and will remain high as long as the count in the counter is a preset number or greater. As soon as the successive signal condition is not realised, the series of gates at the input of the successive shot logic realizes a signal is missing in successive gated periods, the counter and store are reset and are ready for reloading.

Figure 3:
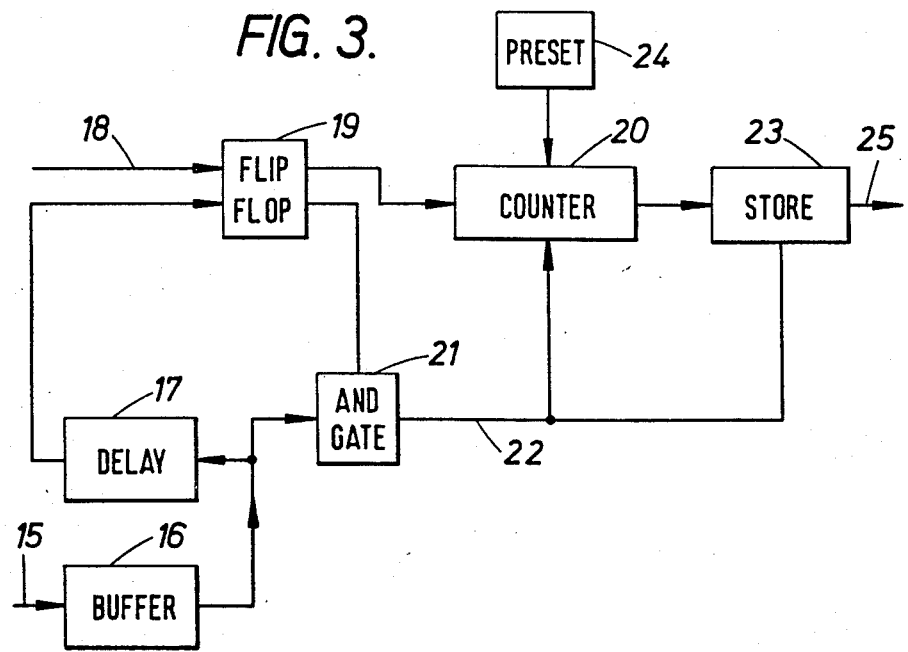
FIG. 3 is a block circuit diagram of the successive shot logic part of the arrangement of FIG. 1.

This operation is illustrated in detail in FIG. 3.

Pulses from the master oscillator are fed into the successive shot logic unit via input 15. The pulses are fed via a buffer 16 partly to a delay 17 which delays the pulse by a few microseconds. It is to be noted that the master oscillator pulse occurs at the same time as the transducer excitation pulse.

A signal from the pulse height discriminator 9 passes via line 18 to a flip flop 19. The signal sets the flip flop 9 which passes one pulse to a counter 20 via one output whilst the other output of flip flop 9 closes 'AND' gate 21 which prevents the next master oscillator pulse from the buffer 16 from passing through the 'AND' gate 21 to the counter and store reset line 22 (thus a count of one is held in the counter 20). The delayed master oscillator pulse from delay 17 resets flip flop 19 and opens 'AND' gate 21. The next signal on line 18 sets flop flop 19 which passes another count to the counter 20, the 'AND' gate 21 is again now closed. This carries on until the preset count in a counter (determined by preset unit 24) is reached and then a signal is fed to a store 23 which gives an output to the successive spiral logic 14. If one or more signals on line 18 are missing, the flip flop 19 is not set, which leaves the 'AND' gate 21 open and allows the master oscillator pulse from buffer 16 to pass through the 'AND' gate and reset the counter 20 and the store 23.

The output from the successive shot logic may also be connected to an audio and/or visual alarm unit 62.

'SUCCESSIVE SPIRAL LOGIC'

When using rotary probe or rotating ultrasonic equipment, customer specifications normally lay down the inspection pitch of the helical scan to be used during production testing. Some specifications ask for 100% coverage while others lay down pitches of 2 or 3 inches or even more. What is not usually defined is the minimum length of discontinuity which should be found. This is an extremely important factor since although at, say, a 1 inch pitch a 1⅛ inches long discontinuity, which gives a response exceeding the equipment trigger level, can be guaranteed to be detected, it is conceivable that if the probe track just happens to pass through a much shorter discontinuity, this may also trigger the equipment. On the other hand, the discontinuity will pass undetected if the probe track does not pass through the discontinuity. The situation is far from ideal.

The present system incorporates a provision to minimize this anomaly, which operates on the basis that primarily inspection pitch of a test should determine the minimum length of discontinuity to be detected.

Figure 4:
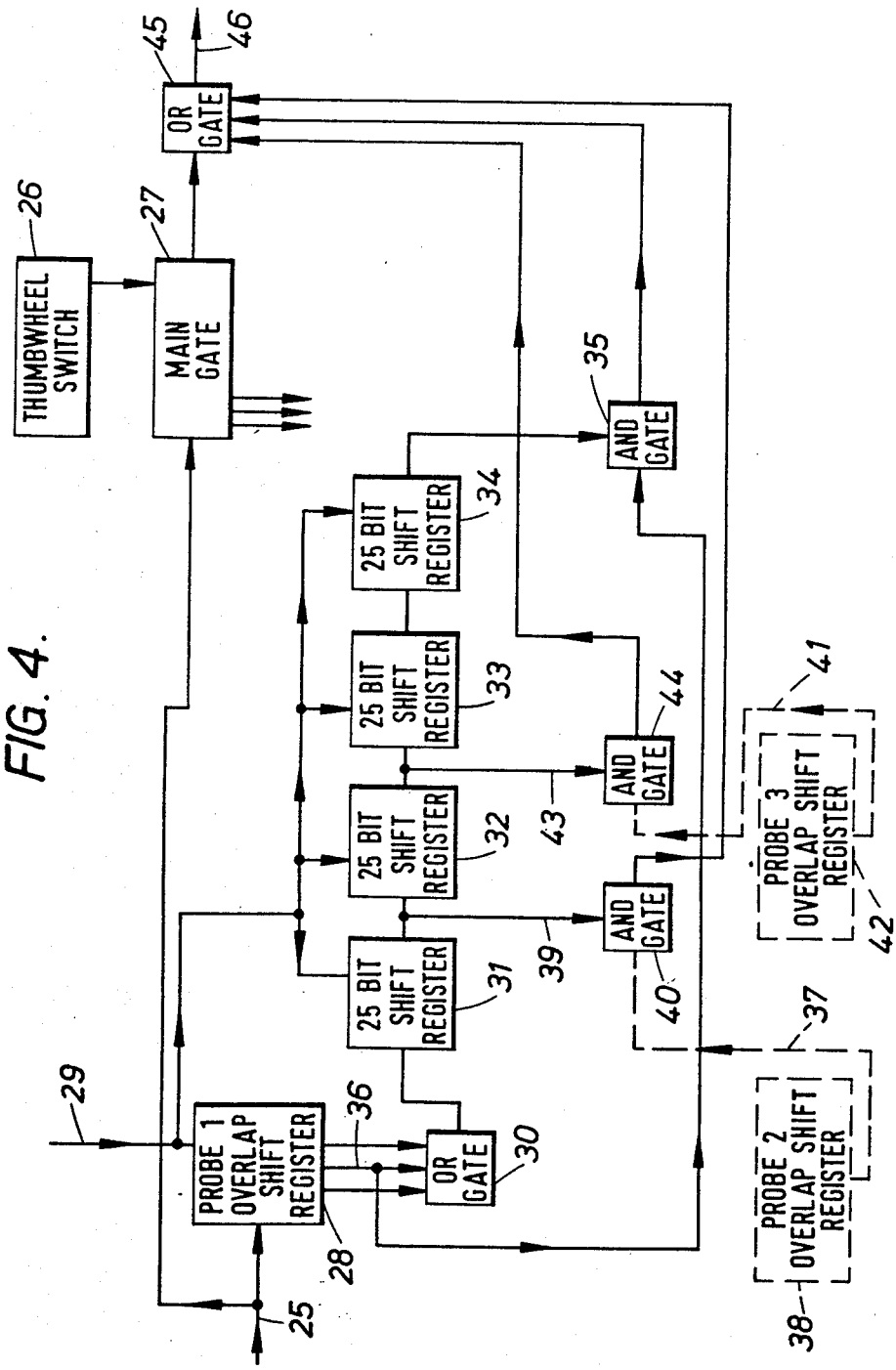
FIG. 4 is a block circuit diagram of the successive spiral logic part of the arrangement of FIG. 1.

In the multi-probe arrangement of the system illustrated the helical pitch of any one shearwave probe, to obtain an overall pitch of ½inch, is 2 inches (½ inch × 4). Thus to allow the successive spiral system to be verstaile enough to be able to sense either short discontinuities, e.g. ¾ inch long, the successive spiral logic operates to accommodate all four probes in relation to one another such that the presence of discontinuities can be detected not only over complete successive spirals but also over ¼ or ½ spirals. The successive spiral logic system is illustrated in detail in FIG. 4.

As there are effectively only four probes (i.e., 4 facing towards and four facing away from direction of rotation), on each set of probes the helical path is that of a four start thread. Considering the situation where any one probe detects the presence of a discontinuity over the pre-set trigger level and which has satisfied the successive shot requirement, any one of the following three conditions is required of the successive spiral logic and this can be selected on the equipment.

1. Any probe is required to detect the same discontinuity one revolution later (at approximately the same circumferential position) as was detected by the same probe on the previous spiral 2. Any one probe is required to detect the same discontinuity ½ a revolution later (at approximately the same circumferential position) as was detected by the probe spaced at 180° round in the direction of rotation 3. Any one probe is required to detect the same discontinuity ¼ of a revolution later (at approx. the same circumferential position) as was detected by the probe spaced at 90° round in the direction of rotation.

It should be noted that the successive spiral system can be bypassed if it is not required.

These requirements are obtained in the following manner:

A signal, which is passed from the successive shot logic 13 on line 25, is passed directly to the output of the successive spiral logic, i.e., successive spiral logic bypassed, if setting of thumbwheel switch 26 is such that 'main' gate 27 is open. If the 'main' gate 27 is closed, then the thumbwheel switch 26 setting will either be on the 1 spiral setting, ½ spiral setting or ¼ spiral setting.

A signal from the successive shot logic is also passed to an 'overlap' shift register 28. The purpose of this register 28 is to ensure that the circumferential position of a discontinuity found on successive spirals (either 1, ½ or ¼ revolution) is located within ±1% of a nominal position (i.e., approximately the same circumferential position).

Taking the situation where the thumbwheel switch 26 setting is on 1 revolution, i.e., any one probe is required to detect the same discontinuity one revolution later, the output signal from the successive shot logic 13 is passed to the input of the overlap shift register 28 (the main 'bypass' gate 27 being closed). This clocks a '1' into the first stage of the overlap shift register. 100 pulses per revolution (provided by the detection of 100 metal studs equispaced around the probe rotor at shift generator 61) are fed to register 28 which shifts this '1' through each stage in turn. The three outputs of the register 28 are passed through the OR gate 30 and fed to the main 4 × 25 bit registers 31, 32, 33 and 34, which, in fact, represent the tube circumference in 1% bands). Thus, after three shift pulses three '1's are progressively shifted through the registers by the 100 pulses per rev. When the same discontinuity is found by the same probe one spiral later a signal is fed to the overlap shift register 28 as before and is shifted through this register. The previous bank of three '1's inserted into the main shift registers will be on the point of exit from the last 25 bit register 34. The output from the last 25 bit register is fed into 'AND' gate 35 with the center stage output 36 of the overlap register 28. Thus, if a discontinuity was found at exactly the same circumferential position on two successive spirals there will be a '1' at the center output 36 of the overlap register 28 when the center '1' of the bank of three '1's in the main registers reaches the output of the last 25 bit stage 34 and an output from the successive spiral logic will result. Coincidence between a '1' in the center stage of the overlap register and any of the three '1's in the main registers thus provides for the ±1% accuracy of circumferential location already mentioned. The ¼ or ½ spiral system perform in a similar manner excepting that the centre stage of the overlap register of the appropriate probe channel is compared with the output of either the first 25 bit register of the probe channel preceding that in question, i.e., the center stage output 37 of the overlap register 38 of probe 2 channel is compared with the output 39 of the first 25 bit register 31 of probe 1 channel at 'AND' gate 40 for ¼ spiral pitch setting or the center stage output 41 of the overlap register 42 of probe 3 channel is compared with the output 43 of the second 25 bit register 32 of the probe 1 channel at 'AND' gate 44 for ½ spiral setting. The coincidence 'AND' gates 40, 44 and 35 are primed for operation by the thumbwheel switch 26 setting and any output from the coincidence 'AND' gate which has been primed, i.e., either single spiral, ½ spiral or ¼ spiral is fed to an OR gate 45 and then passed to the output of the successive spiral logic and then to a system for quadrant marking of detected discontinuity location. As with the successive shot logic 13, the successive spiral logic system 14 consists of 16 channels, one for each probe, internal and external, however the 16 successive shot logic channels are independent in operation, while the successive spiral logic channels are necessarily interlinked when on ¼ or ½ spiral setting to provide the function described.

Having now processed signals returning from the ultrasonic probes to determine:
a. whether they are from internal or external discontinuities
b. whether they exceed the equipment trigger level
c. whether they satisfy a pre-programmed successive shot condition
d. whether they satisfy a pre-programmed successive spiral condition it is now necessary to suitably mark the location of detected discontinuities on the pipe surface as well as recording this information.

Fro marking the position of detected discontinuities a twin quadruple paint gun system is used (not shown), which is mounted downstream of the rotary probe unit. One set of four guns is used for marking the position of detected external discontinuities while the other set marks the position of internal discontinuities. Each set comprises four guns, mounted at 90° intervals such that the tube circumference is divided into four quadrants. Quadrant 1 starts at 45° BTDC (before top dead center), i.e., position of gun No. 1. A discontinuity is marked along with the discontinuity's quadrant location, i.e., in quadrant 1, 2, 3 or 4. In practice if a discontinuity is detected in, say, quadrant 1, the two paint guns at the extremities of quadrant 1 are operated indicating that the discontinuity lies between the two paint marks.

This is achieved in the following manner (referring to FIG. 1):

Taking the internal signal processed information; probe 1 information is passed from successive spiral logic 14 via line 46 to a series of gates in quadrant orientation unit 47 which automatically routes information from probe 1 channel into one of four delay registers 48, 49, 50 and 51 (each one representing one of the four tube quadrants) under the control of shift generator 61. Thus, if probe 1 receives a signal which satisfies all the processing conditions, while probe 1 is scanning through quadrant 1, the processed signal is routed by unit 47 to quadrant 1 delay shift registers 48. The length of the delay is fixed and the shift pulse rate is variable by use of an 'electronic' gearbox. Thus the signal inserted into quadrant 1 shift register is shifted down the delay such that the actual discontinuity will be coincident with the paint system when the signal is at the delay output 52. This signal operates the two guns on either extremity of quadrant 1. Similarly if probe 2, say, detects a signal to quadrant 4 delay 51 which is then shifted down the register and will operate via output 53 the two guns on the extremities of quadrant 4, when the discontinuity is coincident with the paint gun unit.

For recording purposes quadrant orientation unit 47 is connected to recorder logic 12 via lines 54, 55, 56 and 57. Whenever a signal from successive spiral logic 14 is routed to the quadrant orientation unit 47, a signal is fed to the recorder logic 12 indicating that the signal amplitude which has been recorded satisfied the processing conditions and occurred in a specific quadrant, i.e., 1, 2, 3 or 4 internal or external.

Quadrant orientation unit 47 also receives, via lines 58, 59 and 60 similar signals from the internal wall channels of probes 2, 3 and 4. These signals are processed in like manner.

Three duplicate quadrant orientation units serving the same function as above are provided for the remaining 12 probe channels.

Figure 2:
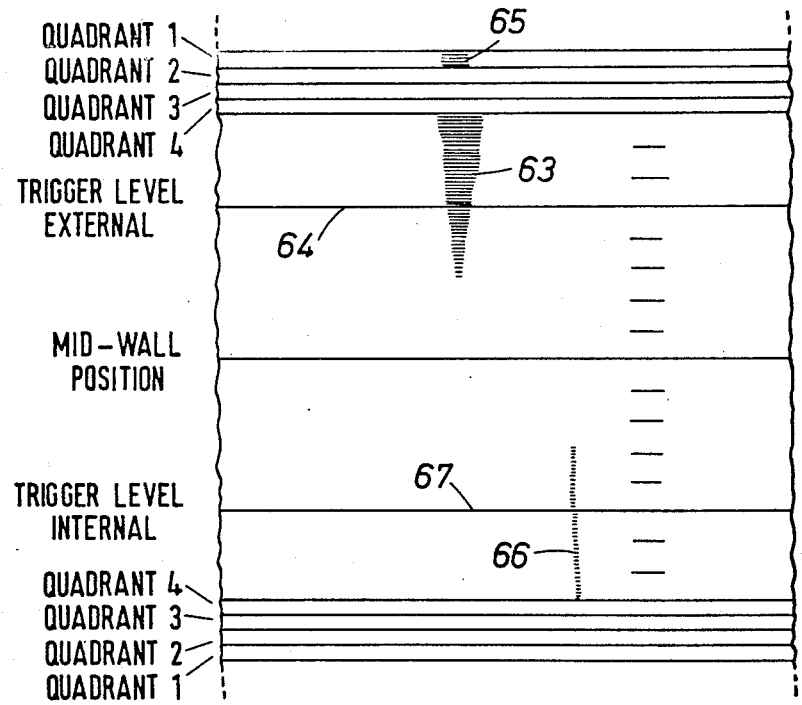
FIG. 2 shows a pictorial representation of defect response.

FIG. 2 illustrates a typical portion of a chart recorder readout display produced by a multi-pen electrostatic recorder of a well known type controlled by the recorder logic unit 12 on receipt of signals from all channels of the system. The discontinuity indicating marking 63 show the presence of signals from one or more of the external wall channels of the system which have exceeded the preset external wall trigger level 64 and have been fed from a pulse height discriminator 9 to the recorder logic 12. Since these signals have also successfully passed through a successive shot logic 13 and a successive spiral logic 14, a marking 65 has been made indicating the quadrant, in this case quadrant 1, within which the discontinuity lies.

The markings 66 similarly show the presence of signals from one or more of the internal wall channels which have exceeded the preset internal wall trigger level 67 and have been fed from a pulse height discriminator to the recorder logic 12. However in this case the signals have not satisfied the successive shot and/or successive spiral logics, so that no quadrant marking is shown.

In the readout display illustrated in FIG. 2, the display moves in a direction parallel to the trigger level lines 64 and 67, at a rate synchronized with a scanning of the probes, so that the relationship between the display and the positions of an object being tested are determinable. The pens of the display are positioned to mark the display, in separate straight lines, after different positions spaced transversely from one another across the display, with respect to the direction of movement of the display. For example, the plurality of pens arranged to provide the marking 63 may be responsive to separate determined signal levels. Similarly, a plurality of pens are provided, each responsive to a separate signal level, for recording the marking 66. While the extent of a markings 63 and 66 in the direction transversely of the direction of movement of the display provide a general indication of the magnitude of the input signal, the equipment in accordance with the invention is primarily employed to relate defects and discontinuities to predetermined tolerance levels.

I claim:
1. Apparatus for testing elongate articles for defects comprising a defect detecting device adapted for helical scanning about the article to be tested; means for marking, upon receipt of defect indicative signals at the device, a pictorial record of the magnitude and the position along the article of the defects shown by the received defect indicative signals; means for applying to defect indicative signals, if they are greater than a predetermined magnitude, predetermined repetition tests; and means for marking on the pictorial record the radial position about the article of defects shown by the received defect indicative signals if they satisfy the predetermined repetition tests.

2. Apparatus as claimed in claim 1 wherein the defect detecting device comprises an ultrasonic pulse testing probe adapted to transmit into the article a plurality of ultrasonic pulses and to receive from the article defect indicative echoes of the pulses from the article.

3. Apparatus as claimed in claim 2 wherein the means for applying to the defect indicative signals predetermined repetition tests includes means for testing whether defect indicative echoes are received from a predetermined number of successive pulses transmitted by the testing probe.

4. Apparatus as claimed in claim 2 wherein the means for applying to the defect indicative signals predetermined repetition tests includes means capable of testing whether defect indicative echoes are received from the pulses transmitted by the testing probe at a predetermined number of successive helical scans past the same radial position about the article.

5. Apparatus as claimed in claim 2 including a plurality of ultrasonic testing probes spaced about the scanning axis and wherein the means for applying to the defect indicative signals predetermined repetition tests includes means for testing whether defect indicative echoes are received from pulses transmitted by a predetermined number of probes during successive scanning movements past the same radial position about the article.

6. Apparatus as claimed in claim 2 including means for determining whether the received defect indicative echoes are greater in magnitude than a predetermined threshold value, said means being adapted to pass signals for pictorial recording and repetition testing only with respect to echoes having a magnitude above said threshold value.

7. Apparatus as claimed in claim 1 wherein the means for marking a pictorial record comprises a multipen electrostatic recorder.

8. Apparatus as claimed in claim 1 including means for marking the article to indicate the longitudinal and radial position of defects shown by received defect indicative signals if they are greater than said predetermined magnitude and if they satisfy the predetermined repetition tests.

9. Apparatus for testing tube like articles including separate apparatus as claimed in claim 1 for testing for defects emanating from the internal wall surface of the article and for testing for defects emanating from the external wall surface of the article.

10. A method of testing elongate articles for defects comprising scanning a defect detecting device in a helical path about the article; marking, upon receipt of defect indicative signals at the device, a pictorial record of the magnitude and position along the article of defects shown by the received defect indicative signals; subjecting received defect indicative signals, if they are greater than a predetermined magnitude, to predetermined repetition test; and marking on the pictorial record the radial position about the article of defects shown by the received defect indicative signals if they satisfy the predetermined repetition tests.

11. A method as claimed in claim 10 wherein the defect detection is carried out by means of an ultrasonic testing probe transmitting a plurality of ultrasonic pulses into the article and receiving from the article defect indicative echoes of the pulses from the article.

12. A method as claimed in claim 11 wherein the step of subjecting the defect indicative signals to predetermined repetition tests includes testing whether defect indicative echoes are received from a predetermined number of successive pulses transmitted by the testing probe.

13. A method as claimed in claim 11 wherein the step of subjecting the defect indicative signals to predetermined repetition tests includes testing whether defect indicative echoes are received from pulses transmitted by the testing probe at a predetermined number of successive helical scans past the same radial position about the article.

14. A method as claimed in claim 11 wherein the defect detection is carried out by means of a plurality of ultrasonic testing probes spaced about the scanning axis and wherein the step of subjecting the defect indicative signals to predetermined repetition tests includes testing whether defect indicative echoes are received from pulses transmitted by a predetermined number of probes during successive scanning movements past the same radial position about the article.

15. A method as claimed in claim 11 including the steps of determining whether the received defect indicative echoes are greater in magnitude than a predetermined threshold value, and passing signals for pictorial recording and repetition testing only with respect to echoes having a magnitude above said threshold value.

16. A method as claimed in claim 11 including the step of marking the article to indicate the longitudinal and radial position of defects shown by received indicative signals if they are greater than said predetermined magnitude and if they satisfy the predetermined repetition tests.

17. A method of testing a tube for defects comprising scanning a plurality of ultrasonic testing probes in a helical path about the tube; using the probes to transmit a plurality of ultrasonic pulses into the tube and to receive from the tube defect indicative echoes of the pulses from the tube; testing whether defect indicative echoes are received from pulses transmitted by a predetermined number of probes during successive scanning movements past the same circumferential position about the tube; and providing an output signal if they are.

* * * * *